United States Patent [19]

Niebes et al.

[11] 4,268,517

[45] May 19, 1981

[54] PHARMACEUTICAL COMPOSITION AND THERAPEUTICAL METHOD FOR TREATING DEGENERATIVE AFFECTIONS OF THE ARTICULAR CARTILAGE

[75] Inventors: Paul J. Niebes, Grez Doiceau; Andras B. Vincze, Brussels; Joseph L. Roba, Ciernont-Houyet; Georges E. Lambelin, Brussels; Daniel M. Matagne, Taviers; Etienne T. Hanon; Michel R. Franz, both of Brussels, all of Belgium

[73] Assignee: Continental Pharma, Brussels, Belgium

[21] Appl. No.: 71,077

[22] Filed: Aug. 30, 1979

[51] Int. Cl.³ .............................................. A61K 31/35
[52] U.S. Cl. .................................................... 424/283
[58] Field of Search ........................................ 424/283

[56] References Cited

FOREIGN PATENT DOCUMENTS 3274 11/1978 European Pat. Off. .
2128207 2/1974 France .

OTHER PUBLICATIONS

Chem. Abst., 87 95790r, (1977).

Primary Examiner—Stanley J. Friedman
Attorney, Agent, or Firm—Cushman, Darby & Cushman

[57] ABSTRACT

A pharmaceutical composition for treating degenerative diseases of the articular cartilage, in particular osteoarthritis and chondromalacia, and of the degenerative processes of the articular cartilage resulting from other diseases, such as rheumatoid arthritis, this composition containing (+) - catechin and/or one of the salts thereof as an active products, said composition being administered orally, rectally, intra-articularly, intravenously or topically.

4 Claims, No Drawings

PHARMACEUTICAL COMPOSITION AND THERAPEUTICAL METHOD FOR TREATING DEGENERATIVE AFFECTIONS OF THE ARTICULAR CARTILAGE

This invention relates to a pharmaceutical composition for treating degenerative affections of the articular cartilage, in particular osteoarthritis and chondromalacia, and also degenerative processes of the articular cartilage resulting from other diseases, such as rheumatoid arthritis.

Degenerative diseases of the cartilage, in particular at the level of the articulations, form a pathology for which no specific treatment exists at the present time.

Treatment of osteoarthritis is mainly carried out by administering analgesic agents and optionally anti-inflammatory agents which only act on the symptoms of the disease. Also, the degeneration of the cartilage in rheumatoid arthritis cannot be directly treated and the therapeutics actually applied (steroidal or not anti-inflammatory agents, gold salts, penicillamine or levamisole) have severe side effects which limit their long-term use.

The essential objects of this invention is to provide a new pharmaceutical composition allowing a specific treatment of the above-mentioned diseases, and furthermore to avoid the side-effects of the treatments known up to now.

To this end, the therapeutical composition according to the invention comprises (+)- catechin and/or one of the salts thereof as active product.

This invention also concerns a particular method of use of this composition, characterized by the fact that said active product is administered at daily doses of 1 to 4 g orally or at daily doses of 5 to 50 mg intraarticularly.

Other details and features of the invention will become apparent from the following description, given by way of non-limitative example, of some specific embodiments of the pharmaceutical composition according to the invention and of the use of the latter.

The (+) - catechin is a natural product of the class of the flavonoids and has the following formula:

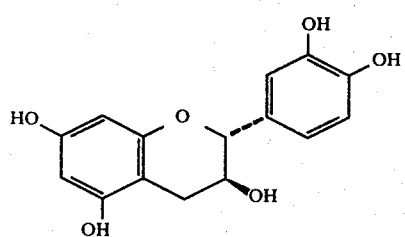

The (+) - catechin /trans-2-(3,4-dihydroxyphenyl)-3,4-dihydro-2H-1-benzopyran-3,5,7-triol/ is mainly obtained by extraction of various vegetal species, in particular from Uncaria Gambir (Rubiaceae).

The (+) - catechin has been known for a long time; as early as 1902 the first publications have been made relating to its extraction. Its chemical structure has been determined in 1925 and its stereochemistry in 1955.

This substance has been used up to now as hepatoprotecting agent due to its effect on enzymes of the respiratory chain and due to its stimulating effect on biosynthesis of ATP.

The use according to the invention of the (+) - cathechin for treating degenerative diseases of the articular cartilage (osteoarthritis, chondromalacia and the like) and degenerative processes of the articular cartilage resulting from other diseases such as rheumatoid arthritis, is a therapeutical use based on new biochemical and pharmacological observations.

According to the invention, biochemical observations (in vitro) have allowed to prove that (+) - catechin added to a solution of collagen extracted from rat skin allows to accelerate the formation of collagen fiber: at $3.9 \times 10^{-4}M$, (+) - catechin increases the fibrillation rate by 50%.

The technique consists of measuring in function of time, the collagen polymerization at 37° C. by reading at 540 nm the optical density of an incubation medium containing 0.75 mg/ml of collagen solubilized in a phosphate buffer (pH=7.6).

On the other hand, degradation of collagen fibers due to collagenase is inhibited by 50% with $5.8 \times 10^{-3}M$ of (+) - catechin. The technique consists of incubating for 24 hours in a tris-HCl buffer (pH 7.2) insoluble collagen fibers of Achilles tendon of bovine origin in the presence of bacterial collagenase. The amino-acids which are released free are measured by colorimetric reaction with ninhydrin.

Furthermore, it has been found that (+) - catechin at the concentration of $10^{-4}M$ inhibits the spontaneous degradation of the proteoglycans of the cartilage isolated from rabbit ear.

Studies made on cultures of fibroblasts of rat embryo skin have allowed to reproduce a lathyrogen effect by addition of $\beta$-aminopropionitrile. The treated fibroblasts produce collagen containing proportionally more $\alpha$ monomer chains than $\beta$ dimer. The (+) - catechin, at a concentration of $5.10^{-4}M$ in the culture medium and in the presence of $\beta$-aminopropionitrile, increases the proportion of insoluble collagen and restores a normal ratio between $\alpha$ and $\beta$ chains. The protecting effect of the (+) - catechin on collagen is explained by an increase of the number of cross-links.

At the final concentration of $5.10^{-4}M$, (+) - catechin does not quantitatively affect the synthesis of proteins or collagen in control cultures which have not been submitted to the lathyrogen.

In other respects, it has been shown that (+) - catechin inhibits the synthesis of prostaglandin $PGE_2$. As an example, (+) - catechin inhibits by 50% the synthesis of $PGE_2$ at a dose of $7.4 \times 10^{-5}M$. Indomethacin has the same effect at a concentration of $7.10^{-6}M$ and phenylbutazone at $4.10^{-4}M$. This activity may be considered as a significant anti-inflammatory effect of the (+) - catechin.

These biochemical observations have been confirmed in an animal model of degenerative pathology of articular cartilage. In rats made arthritic by the adjuvant method, (+) - catechin administered at 200 mg/kg/day orally, decreases the development osteoporosis at the level of affected articulations and prevents degradation of the connective tissue. These effects are shown by a suppression of the increase of urinary excretion of hydroxyproline.

These results are shown in the following tables 1 and 2.

TABLE I

Radiographic scores of osteopororis of the external malleolus of the tibia

| | GROUPS | | |
|---|---|---|---|
| WEEKS | I NON ARTHRITIC | II ARTHRITIC | III ARTHRITIC + CATHECHINE 200 mg/kg. |
| 1 | 2.00 ± 0.00 | 2.00 ± 0.00 | 2.00 ± 0.00 |
| 2 | 2.00 ± 0.00 | 2.00 ± 0.00 | 2.05 ± 0.05 |
| 3 | 2.05 ± 0.04 | 2.15 ± 0.11 | 2.37 ± 0.24 |
| 4 | 2.03 ± 0.003*** | 3.29 ± 0.40 | 2.39 ± 0.16 |
| 5 | 2.03 ± 0.03** | 3.11 ± 0.41 | 2.69 ± 0.33 |
| 6 | 2.05 ± 0.04*** | 2.92 ± 0.24 | 2.68 ± 0.25 |
| 7 | 2.03 ± 0.03* | 2.50 ± 0.27 | 2.00 ± 0.00 |

A score of 1 (normal) to 4 is attributed to each posterior member as a function of the density of the bone at the level of the external malleolus of the tibia. These examinations are carried out according to a blind method on coded radiographies. The results given are the mean values (± S.E.M.) of the sums of scores per animal. The mean values marked *, , * are significantly different from those of controls at the threshold α = 0.05, 0.01 or 0.001 respectively.

TABLE II

Urinary hydroxyproline (µg/mg creatinin, mean values ± S.D.)

| | GROUPS | | |
|---|---|---|---|
| WEEKS | I NON ARTHRITIC CONTROLS (n = 6) | II ARTHRITIC CONTROLS (n = 7) | II ARTHRITIC + CATHECHINE 200 mg/kg (n = 7) |
| −1 | 46.7 ± 7.0 | 47.6 ± 6.6 | 47.5 ± 4.3 |
| 1 | 39.0 ± 2.1* | 47.6 ± 6.8 | 40.2 ± 4.4 |
| 2 | 33.0 ± 6.4** | 55.0 ± 10.0 | 49.2 ± 15.5 |
| 3 | 33.1 ± 3.5** | 60.4 ± 18.5 | 40.6 ± 4.9* |
| 4 | 27.6 ± 5.0** | 61.3 ± 21.4 | 36.1 ± 5.3* |
| 5 | 30.9 ± 5.5** | 65.6 ± 21.2 | 39.5 ± 7.3* |
| 6 | 30.7 ± 4.2*** | 65.5 ± 17.8 | 37.7 ± 9.7** |
| 7 | 33.0 ± 6.1** | 65.5 ± 24.0 | 38.4 ± 6.3* |
| 8 | 22.8 ± 7.8*** | 66.1 ± 18.5 | 42.6 ± 9.7* |
| 9 | 25.2 ± 6.4* | 48.8 ± 19.5 | 34.7 ± 9.8 |

The mean values significantly differing from the values of arthritic controls are marked *,  or * respectively for α = 0.05, 0.01 and 0.001.

The results obtained in rats confirm that the protecting properties on the proteoglycans and the collagen fibers, made evident in vitro, lead to a therapeutical effect on the radiologic and biochemical evoluton of the articular lesions. This allows an original use of (+) - catechin for a basic treatment of degenerative affections of the articular cartilage.

As a conclusion, (+) - catechin exerts a basic protecting action on the cartilage against spontaneous degenerative phenomena and against those due to chronic inflammatory processes.

The recommended doses for the preferred modes of administration are 1 to 4 g, preferably 2 to 3 g/day orally or rectally; and they are 5 to 50 mg/day intraarticularly or intraveneously.

If topically administered, the recommended doses are of about 100 mg to 2 g for each application.

The (+) - catechin may be administered in association with various pharmaceutical excipients orally, parenterally, rectally, topically or intra-articularly.

For oral administration, dragees, granules, lozenges, capsules, tablets, solutions, syrups, emulsions, or film coated tablets are used with appropriate additives or excipients. These galenical formulations may liberate the active principle in a normal or a time-programmed way. For parenteral or intra-articular administration, the salts of (+) - catechin may be dissolved in a suitable aqueous solution. For rectal administration, suppositories or rectal capsules are used.

For topical administration, creams, pastes, gels and ointments are prepared.

This active compound may be administered on its own or in association with other active products having a similar or different activity. The (+) - catechin may be administered as various forms. Following examples are not limitative and relate to galenical formulations containing (+) - catechin.

| Film coated tablets. | |
|---|---|
| (+) - Catechin hydrate | 575 mg. |
| Soluble Starch | 57 mg. |
| Magnesium stearate | 3 mg. |
| Methocel*, 60 HG 50 cps | 5.8 mg. |
| Glycerin | 1.1 mg. |
| Opaspray*, white | 3.0 mg. |
| Opaspray*, orange K-1-3497 | 1.8 mg. |
| | 646.7 mg. |

*registered trade mark

This tablet can be made by a direct compression way.

| Injectable solution, i.m. and i.v. | |
|---|---|
| (+) - catechin | 55 mg. |
| Ethanol | 275 mg. |
| Sodium sulfite | 1 mg. |
| Benzyl alcohol | 75 mg. |
| Lysine | to pH 7.0 |
| Deoxygenated distilled water | ad 5 ml |

| Injectable solution, intra-articular and i.v. | |
|---|---|
| (+) - catechin | 75 mg. |
| Lysine | 37.8 mg. |
| Hydrochloric acid | to pH 7.0 |
| Benzyl alcohol | 100 mg. |
| Deoxygenated distilled water | ad 5 ml. |

| Cream | |
|---|---|
| (+) - catechin | 10 g |
| Glycerin | 2 g. |
| Perhydrosqualene | 8 g. |
| Liquid paraffin | 8 g. |
| Solid paraffin | 6 g. |
| Cetylstearyl alcohol | 4.5 g. |
| Sodium cetylstearylsulfate | 0.5 g. |
| Emulgine B-3* | 2 g. |
| Aluminium stearate | 0.3 g. |
| Citric acid | 0.1 g. |
| Nipasept* | 0.2 g. |
| Distilled water | ad 100 g. |

*Registered trade mark.

The meaning of some terms used in above-given galenical formulations is given hereinafter:

Opaspray, white: lacquer for coating, containing titanium oxide and hydroxypropylmethyl cellulose.

Opaspray, orange: lacquer for coating, containing iron oxides and hydroxypropylmethyl cellulose.

Emulgine B-3: cetylstearic alcohol containing ethylene oxide.

Nipasept: mixture of methyl, ethyl and propyl esters of p-hydroxybenzoic acid.

The following indicative example, illustrates the method for extracting (+) - catechin within the scope of the invention.

In a reactor, 23.9 kg of Block Gambir and 190 l of ethyl acetate (AcOet) were heated at 65°–70° C. for 1 hour. Then 1.5 kg of animal charcoal were added and stirred for 1 hour at 65°–70° C. The solution so obtained was filtered through "Nutsche" with a Celite bed (1 kg of Celite) and the cake washed with 2×20 liters of AcOEt. The filtrate was concentrated by heating under vacuum (59°–63° C./70 mm Hg). 148 l of permutated water were added and AcOEt was removed by azeotropic distillation with return of water into the reactor. 1.26 kg of animal charcoal was added to the aqueous solution which was then heated, agitated and hot filtered on a Büchner filter. The filtrate was cooled to 5° C. under nitrogen.

The (+) - catechin was precipitated as a yellowish powder, filtered through "Nutsche", and washed with iced permutated water. The cake was centrifuged and the product dried under vacuum at ±35° C.

The weight of (+) - catechin obtained was 8.5 kg with a humidity of ±15% (yield with respect to Block Gambir: 35.55%). The (+) - catechin was identified by infrared spectrometry and the water content was determined by the Karl-Fischer method.

We claim:

1. A method for treating a degenerative disease of the articular cartilage which comprises administering to a host suffering from said degenerative disease, an effective amount of (+)-catechin.

2. A method as claimed in claim 1 wherein the (+)-catechin is administered at daily doses of 1 to 4 g orally or rectally.

3. A method as claimed in claim 1 wherein the (+)-catechin is administered at daily doses at 5 to 50 mg intra-articularly or intravenously.

4. A method as claimed in claim 1 wherein the (+)-catechin is administered topically at doses of about 100 mg to 2 g.

* * * * *